United States Patent [19]

van Wersch et al.

[11] 4,112,077
[45] Sep. 5, 1978

[54] DIAZABORINES AND DRUG COMPOSITIONS

[76] Inventors: Hubert Maria Agnes van Wersch, Ruysdaelstraat 33, Kerkrade, Netherlands; Siegfried Herrling, Dohlenweg 33 (BRD), Stolberg; Heinrich Muckter, Am Chorusberg 51 (BRD), Aachen, both of Germany

[21] Appl. No.: 708,361

[22] Filed: Jul. 26, 1976

[30] Foreign Application Priority Data

Jul. 30, 1975 [DE] Fed. Rep. of Germany ....... 2533918
May 11, 1976 [DE] Fed. Rep. of Germany ....... 2620776
May 11, 1976 [DE] Fed. Rep. of Germany ....... 2620777

[51] Int. Cl.$^2$ ............................................. A61K 31/69
[52] U.S. Cl. .................................. 424/185; 260/502.3
[58] Field of Search ........................ 260/462 C, 502.3; 424/185

[56] References Cited

U.S. PATENT DOCUMENTS 3,714,206   1/1973   Lweifall et al. ................... 260/397.7

*Primary Examiner*—Helen M. S. Sneed
*Attorney, Agent, or Firm*—Weiser, Stapler & Spivak

[57] ABSTRACT

Derivatives of 1-hydroxy-benzo-2,3,1-diazaborines which are substituted in the 2-position by a sulfo group linked to a defined aliphatic radical like alkyl or alkylene and salts of such compounds. The compounds are highly effective against gram-negative bacteria in pharmaceutical compositions containing these diazaborines. The new compounds are prepared by reacting o-formyl phenyl boric acid with the respective aliphatic sulfonic acid hydrazide.

30 Claims, No Drawings

DIAZABORINES AND DRUG COMPOSITIONS

The invention relates to new derivatives of 1-hydroxy-benzo-2,3,1-diazaborine, a process for their preparation, and therapeutic compositions. The compositions of the invention are especially effective antibacterial compositions against gram-negative bacteria. U.S. Pat. No. 3,714,206, of Jan. 30, 1973, to Huemer et al, entitled BENZO-2,3,1-DIAZABORINES and in British patent specification Nos. 1,182,132 and 1,202,219 (and corresponding patents in other countries), there are disclosed 1-hydroxy-2,3,1-diazaborine derivatives which are linked in the 5,6-position to a phenylene-, thienylene- or naphthylene ring and which are substituted in the 2-position with a sulfo group linked to an unsubstituted or, preferably, substituted aromatic or heterocyclic radical. These compounds are useful antimicrobial agents and are especially effective against gram-negative bacteria. Preferred members of the known group of substances are derivatives of 1-hydroxy-benzo-2,3,1-diazaborines.

Although 2-arylsulfonyl substituted 2,3,1-diazaborine derivatives have been known for several years, there is no disclosure of 1-hydroxy-sulfonyl-benzo-2,3,1-diazaborines, which are 2-alkyl-substituted, and which are antibacterially active.

A new class of derivatives of 1-hydroxy-benzo-2,3,1-diazaborines has now been discovered, the members of which are, unexpectedly, useful as antimicrobial agents. The class of compounds of the invention is represented by the the general formula I

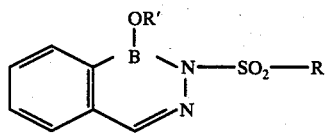

wherein R is acyclic alkyl or alkylene which may be branched or straight, has 2 to 5 carbon atoms and which may be substituted by 1 to 3 halogen atoms, preferably chlorine atoms, or R represents a mono-, di- or tri-halogen methyl radical and wherein R' is a hydrogen atom or a pharmaceutically acceptable cation, preferably an alkali metal cation.

In preferred compounds of the class, R may have 3 to 4 carbon atoms or may have 1 to 3 carbons being substituted by 1 to 3 halogen atoms, preferably chlorine. R may also advantageously be an alkylene such as allyl, vinyl or crotyl. Preferred members also include those where R is a mono-, di- or tri-halo-substituted methyl or ethyl radical. Preferred members of the class of chloro-substituted R constituents are those where R is chloromethyl, monochloro-substituted, or dichloropropyl.

For a better appreciation of the subject matter of this invention, it should be kept in mind that while gram-positive pathogens were an important cause of bacterial infections in mammals in the 1950's, gram-negative bacteria have become an increasingly important and pernicious cause of infections during the last decade. Several studies have shown that a large proportion of bacterial infections in United States hospitals are induced by gram-negative pathogens.

While it is recognized that there is an adequate supply of chemo-therapeutic drugs available for the control of gram-positive bacteria, that effective in the control of gram-negative bacteria leaves very much to be desired.

While the benzo-2,3,1-diazaborines of U.S. Pat. No. 3,714,206 are a significant contribution to the pharmaceutical and medical arts in human and veterinary therapy, it has been quite unexpected to find another class of boron containing heterocyclic compounds specifically substituted in the 2-position as defined herein, which are so effective against gram-negative bacteria, in particular *E.coli.* Furthermore, the antimicrobial compounds of the invention unexpectedly differ in their low toxicity and effectiveness when compared to compounds structurally analogous or homologous.

The new compounds of formula I have pronounced controlling activity against microorganisms. This activity has been demonstrated not only in vitro but also in effected animals on parenteral or oral administration of the compounds, this in accordance with standard test methods adapted and recognized by those skilled in the art as being properly correlated with human utility.

The compounds of the invention are effective in controlling gram-negative bacteria such as *Escherichia coli, Salmonella typhimurium, Proteus vulgaris, Proteus mirabilis,* and others.

The compounds of the invention are administered in an amount effective to control the gram-negative bacteria and less than the amount which is toxic to the subject treated. A convenient therapeutic daily dose is in the range of about 250 to about 1500 mg. Smaller dosage cause generally a slower control of the bacteria.

Typical of the compounds of the class are very active antimicrobial agents, especially against gram-negative bacteria, in particular *E.coli.* For instance, the following values of the $CD_{50}$ were determined on administering the listed compounds of formula I, in which R is as defined in the following Table I, Antimicrobial Activity, and wherein R' is sodium to mice infected with the bacteria shown.

Table I

| | ANTIMICROBIAL ACTIVITY | |
|---|---|---|
| R | *E. coli* p. o. | (CD 50 mg/kg) s. c. |
| 1  $C_2H_5$— | 11.0 | 9.8 |
| 2  n-$C_3H_7$— | 7.0 | 6.7 |
| 3  i-$C_3H_7$— | 12.5 | 9.2 |
| 4  n-$C_4H_9$— | 11.2 | 5.85 |
| 5  $CH_3$<br>     \<br>      CH—$CH_2$—<br>     /<br>   $CH_3$ | 8.85 | 10.6 |
| 6  $CH_2$=CH—$CH_2$— | 13.2 | 13.2 |
| 7  Cl—$CH_2$— | 12.4 | 11.8 |
| 8  $CH_3$—CH—<br>          \|<br>          Cl | 17.7 | 14.0 |
| 9  Cl—$CH_2$—$CH_2$—$CH_2$ | 22.7 | 21.8 |

$CD_{50}$ = Dose in mg of compound/kg of mouse body weight which cures the infection in 50% of the animals. The compounds of the invention also show effectiveness against other gram-negative bacteria. For instance, the $CD_{50}$-values for compound 2 (R=$nC_3H_7$—) against B. proteus are 18.7 mg/kg under per oral ("p.o.") administration and 11.7 mg/kg under subcutaneous ("s.c.") administration and against Klebsiella pneumoniae 11.3 mg/kg p.o. and 6.75 mg/kg s.c.

It is noteworthy that the —$CH_3$ and the higher alkyl analogs are inadequately effective in the control of the bacteria. For comparison, also, the compound of Example 58 of U.S. Pat. No. 3,714,206, 1-hydroxy-2(2'-chloro-4'-aminophenyl sulfonyl) benzo-2,3,1-diazaborine, has the following effectiveness, as shown in Table II.

Table II
COMPARATIVE ANTIMICROBIAL ACTIVITY

| R | E. coli p. o. | (CD$_{50}$ mg/kg) s. c. |
|---|---|---|
| CH$_3$— | 100 | 100 |
| n-C$_6$H$_{13}$— | 100 | 42.3 (toxic) |
| n-C$_8$H$_{17}$— | >1600 | >400 (toxic) |
| n-C$_{12}$H$_{25}$— | >1600 | >1600 |
|  | 36 | 13,5 |

It is apparent that the class of compounds of the invention is highly effective in the control of gram-negative bacteria. In the compounds of the invention, it is preferred that R in formula I contain only one halogen atom, especially one chlorine atom.

Where R is alkylene of more than 2 carbon atoms, the double bond therein can be positioned between any two of the carbon atoms. It is, however, preferred that the double bond be positioned between carbon atoms 2 and 3 in the alkylene group.

The compounds of the invention are prepared by condensing o-formyl phenyl boric acid with a sulfonic acid hydrazide of formula II $$H_2N—NH—SO_2—R \qquad (II)$$

wherein R has the same definition as above. In the resulting product R' represents hydrogen. This compound can be converted to its corresponding salts, in which R$_1$ is a pharmaceutically acceptable cation.

As many of the compounds of formula II are relatively unstable, it is advisable to prepare them, for instance, by reacting the corresponding sulfonic acid chloride with hydrazine hydrate and introduce them directly, without purification, as crude products into the process of the invention, and then proceed as described.

Preferably the sulfonic acid hydrazide of formula II is reacted with the o-formyl-phenyl boric acid in the presence of a solvent or a suspending diluent, such as an alkanol, dioxane, tetrahydrofurane, an aromatic hydrocarbon, for instance benzene or toluene, and if required at elevated temperature.

Compounds of formula I in which R represents a haloalkyl radical containing 2 to 5 carbon atoms and 1 to 2 halogen atoms may also be prepared by adding a halogen or a hydrogen halide to the double bond in the alkylene group of a compound of formula I in which R represents an alkylene group containing 2 to 5 carbon atoms and in which R' is hydrogen.

In this reaction the alkylene group containing starting material is dissolved, for instance, in glacial acetic acid or in a halo-alkane such as chloroform or dichloro methane and treated — preferably while illuminating — with the halogen, for instance, chlorine or bromine, until the double bond is saturated. Especially in case of adding a hydrogen halide such as hydrogen chloride or hydrogen bromide, it is advisable to heat the reaction mixture in order to speed up the reaction, such as in a temperature range of 30° C. to 80° C.

Due to the hydroxyl group linked to the boron atom, the compounds of formula I, wherein R' is hydrogen, are capable of forming salts with bases, in which salts R' is a cation. For instance, solutions of such salts can be prepared in that a compound of formula I can be shaken with dilute (e.g., 0.1 to about 2 normal) sodium or potassium hydroxide, aqueous ammonia solutions or with solutions of organic bases, such as triethylamine, ethylene diamine, diethanol amine and so on. Especially the alkali salts may be easily isolated from such solutions, for instance by freeze drying. When organic solutions are used, they are conveniently 5 to 10% solutions.

For further details about the method of preparation of the compounds of the invention, including conditions and reactants, reference is made to U.S. Pat. No. 3,714,206 which is incorporated herein by reference for convenience to one skilled in the art.

Since the compounds of the invention exhibit only low toxicity, they are very well suited for therapy or control of gram-negative infections in man and in animals. They can be administered orally, parenterally, topically or rectally.

The following examples are merely illustrative of the invention; they are not to be construed as limitation. All temperatures are uncorrected.

EXAMPLE 1

The alkyl sulfonic acid hydrazides of formula II are prepared by the reaction of the corresponding sulfonic acid chloride with hydrazine hydrate analog as disclosed in Can. J. Chem. 33 (1955) 1250–55 (where R is ethyl, n-propyl, isopropyl) and in accordance with Canadian Pat. No. 511,584 (for R = n-butyl, isobutyl and n-amyl). The compounds are oily-like, relatively unstable substances which are used in crude state as starting materials in the process of the invention.

Most of the alkyl sulfonic acid chlorides are prepared in accordance with J. Org. Chem 16 (1951) 621–25. The isopropyl sulfochloride analog was prepared as described in Chem. Ber. 100 (1967) 1696–1700.

EXAMPLE 2

0.05 mol of o-formyl phenyl boric acid is dissolved in 100 ml of ethanol. While stirring, 0.05 mol of the selected alkyl sulfonyl hydrazide is added at room temperature. The temperature is slowly raised to boiling and after approximately 5 minutes of boiling, the reaction mixture is allowed to cool to 30° C. The mixture is evaporated and the residue stored at about 0° C., whereupon the desired products crystallize. On recrystallization from methanol, the product of formula I, wherein R' is hydrogen, is obtained in pure form.

In the table below, melting points (m.p.) and yields (in % of the theoretical yield) for compounds of formula I (R' = H) having different substituents for R are shown:

| R | m.p. in ° C | Yield |
|---|---|---|
| C$_2$H$_5$— | 111 – 113 | 69.5 |
| CH$_3$(CH$_2$)$_2$— | 84 – 85 | 38.1 |
| CH$_3$\\_CH—/CH$_3$ | 101 – 103 | 55.6 |
| CH$_3$(CH$_2$)$_3$— | 48 – 49 | 53.0 |

-continued

| R | m.p. in °C | Yield |
|---|---|---|
| 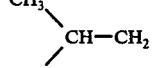 | 62 – 63 | 53.4 |
| $CH_3-(CH_2)_4-$ | 51 | 43.5 |

EXAMPLE 3

The procedure is as described in Example 2. However, 0.05 mol of the selected alkylene sulfonyl hydrazide, which is prepared in the same manner as described in Example 2, is used instead of the alkyl sulfonyl hydrazide.

The table below shows melting points, yields and solvents used in recrystallization of different compounds of formula I (R' = H) prepared in this way:

| R | recrystallization solvent | m.p. in °C | yield |
|---|---|---|---|
| $CH_2=CH-CH_2-$ | ethanol | 101 – 103 | 57 |
| $CH_2=C-CH_2-$<br>$\quad\ \,\vert$<br>$\quad\ \,CH_3$ | acetone | 140 – 142 | 73.5 |

EXAMPLE 4

A mixture of 10 ml of hydrazine hydrate and 90 ml of ethanol is chilled to 0° C. and then, while stirring, a solution of 15 g of chloromethyl sulfonyl chloride in 10–15 ml of cold (0° C.) ehtanol is added. The mixture is stirred for 30 minutes, the hydrazin-hydrochloride filtered off and the filtrate evaporated. The oily-like residue is dissolved in 25 ml of ethanol. This solution is added to a solution of 15 g o-formyl phenyl boric acid in 150 ml of ethanol. The further procedure is as described in Example 2. The 1-hydroxy-2-chloromethyl-sulfonyl-benzo-2,3,1-diazaborine thus obtained is recrystallized from ethanol and melts at 174–175° C. The yield is 32% of the theoretical yield.

EXAMPLE 5

The procedure is as described in Example 2. However, 0.05 mol of the selected halogen alkyl sulfonyl hydrazide, which is prepared analog as described in Example 2, is used instead of the unsubstituted alkyl sulfonyl hydrazide used in Example 2.

The melting points and yields of the products obtained are shown in the following table:

| R | m.p. in °C | yield |
|---|---|---|
| $CH_3-CH-$<br>$\quad\ \,\vert$<br>$\quad\ \,Cl$ | 116 – 118° | 43.4% |
| $Cl-CH_2-CH_2-CH_2-$ | 102 – 104° | 57.0% |

EXAMPLE 6

0.05 mol of a compound of formula I (R' = hydrogen), as for instance, 12.5 g of 1-hydroxy-2-allyl-sulfonyl-benzo-2,3,1-diazaborine, is added at room temperature, while stirring, to 100 ml of water. There is added 2N-sodium hydroxide solution until the pH is 7 whereupon a solution is obtained which is filtered. The filtrate on lyophilization gives the sodium salt of the benzo-2,3,1-diazaborine derivative used, in form of a white powder which is easily soluble in water.

Following the procedure as described in the examples as supplemented by the description, the 1-hydroxy-benzo-2,3,1-diazaborine derivatives having the following substituents in the 2-position of the ring are obtained.

| $R-SO_2-$ | $R-SO_2-$ |
|---|---|
| bromo methyl sulfonyl | $(Br-CH_2-SO_2-)$ |
| dichloro methyl sulfonyl | $(Cl_2-CH-SO_2-)$ |
| trifluoro methyl sulfonyl | $(CF_3-SO_2-)$ |
| trichloro methyl sulfonyl | $(CCl_3-SO_2-)$ |
| vinyl sulfonyl | $(CH_2=CH-SO_2-)$ |
| 2-chloro ethyl sulfonyl | $(Cl-CH_2-CH_2-SO_2-)$ |
| 1,2-dichloro ethyl sulfonyl | $(Cl-CH_2-CH-SO_2-)$<br>$\qquad\qquad\ \ \,\vert$<br>$\qquad\qquad\ \ \,Cl$ |
| 1,2-dibromo ethyl sulfonyl | $(Br-CH_2-CH-SO_2-)$<br>$\qquad\qquad\ \ \,\vert$<br>$\qquad\qquad\ \ \,Br$ |
| 2,2-dichloro ethyl sulfonyl | $(Cl_2-CH-CH_2-SO_2-)$ |
| 2,2,2-trifluoro ethyl sulfonyl | $(CF_3-CH_2-SO_2-)$ |
| crotyl sulfonyl | $(CH_3-CH=CH-SO_2-)$ |
| 1,3-dichloro propyl sulfonyl | $(ClCH_2-CH_2-CH-SO_2-)$<br>$\qquad\qquad\qquad\ \ \,\vert$<br>$\qquad\qquad\qquad\ \ \,Cl$ |
| 1,2,3-trichloro propyl sulfonyl | $(ClCH_2-CH-CH-SO_2-)$<br>$\qquad\qquad\ \ \,\vert\ \ \ \vert$<br>$\qquad\qquad\ \ \,Cl\ \ Cl$ |
| buten-(1)-yl sulfonyl | $(CH_3-CH_2-CH=CH-SO_2-)$ |
| buten-(2)-yl sulfonyl | $(CH_3-CH=CH-CH_2-SO_2-)$ |
| buten-(3)-yl sulfonyl | $(CH_2=CH-CH_2-CH_2-SO_2-)$ |
| 2-methyl propen-(1)-yl sulfonyl | $(CH_3-C=CH-SO_2-)$<br>$\qquad\qquad\vert$<br>$\qquad\qquad CH_3$ |
| penten-(1)-yl sulfonyl | $(CH_3-CH_2-CH_2-CH=CH-SO_2-)$ |
| penten-(2)-yl sulfonyl | $(CH_3-CH_2-CH=CH-CH_2-SO_2-)$ |

The new compounds of formula I of the invention possess, as described above, high activity against gram-negative bacteria. It is also noteworthy that the compounds of the invention exhibit only low toxicity and hence are very well suited for therapy or control of gram-negative infections in warm-blooded mammals such as man and animals. They can be administered orally, parenterally, topically or rectally. The low toxicity of the compounds of the invention is even evident on prolonged administration and they do not produce adverse side effects.

Regarding the antimicrobial compositions of the invention they can be prepared and administered in accordance with well accepted medical and pharmaceutical practices. For oral administration they can be made up into powders, tablets or other solid state preparations. They can also be used in aqueous or saline suspensions or solutions for parenteral administration like intramuscular injections, or other aqueous solutions, particularly those in which R' is an alkaline metal, which salts are water soluble.

Since other aspects of the preparation and administration of the pharmaceutical compositions incorporating the compounds of the invention are known from prior literature, reference is made herein again to U.S. Pat. No. 3,714,206, particularly those sections dealing with pharmaceutical compositions of columns 26 and 27 and others, which are incorporated herein by reference. Conveniently, the compositions of the invention contain from 1% to about 100% by weight of the total weight of the composition, of the effective compound of formula I of the invention.

The new compounds have proved to be especially valuable for topical administration as antimicrobial agents, for instance, in the form of salves, ointments, creams, pastes, cerates, plasmas, liniments, dusting powders, emulsions, lotions, and the like topically applicable compositions. Incorporation of the compounds into adhesive plasters and tapes, especially those provided with pads such as the so-called "Band-Aids" and the like is also possible. They may be incorporated in soaps and other detergents, if desired, in combination with other active agents, for instance, with antibacterial agents which are effective against gram-positive bacteria. Rectal or vaginal administration, for instance, in the form of rectal and vaginal suppositories or urethral bougies whereby the vehicle may be cocoa butter (theobroma oil), glycerinated gelatin, mixtures of polyethylene glycols, or other conventionally used suppositories is also possible.

These and other pharmaceutical compositions are prepared in a manner known per se and with pharmaceutical incipients as they are conventionally used for this purpose. It may be mentioned that the new compounds and their pharmaceutical compositions have proved of value not only in human medicine but also in veterinary medicine.

The compositions of the invention are prepared as shown in the examples of U.S. Pat. No. 3,714,206.

We claim:

1. New derivatives of 1-hydroxy-benzo-2,3,1-diazaborine of the formula

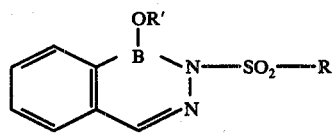

herein R is an acyclic alkyl or alkenyl radical having 2 to 5 carbon atoms, or R is a mono-, di- or tri-halogen methyl radical and wherein R' is a hydrogen or a cation which together with and in formula (I), is pharmaceutically acceptable and effective to control gram-negative bacteria.

2. The compound of claim 1 wherein R is an acyclic alkyl or alkenyl radical having 3 to 4 carbon atoms.

3. The compound of claim 1 wherein the alkyl is a straight chain.

4. The compound of claim 1 wherein the alkyl is branched.

5. The compound of claim 1 wherein R is alkenyl of 2 to 5 carbon atoms.

6. The compound of claim 2 wherein the alkyl is of 1 to 3 carbon atoms.

7. The compound of claim 1 wherein the cation is an alkali metal.

8. The compound of claim 6 wherein R is substituted by 1 to 3 halogen atoms.

9. The compound of claim 7 wherein the alkali metal is sodium.

10. The compound of claim 1 wherein R is substituted with a single chlorine atom.

11. The compound of claim 1 wherein R is halomethyl.

12. The compound of claim 1 wherein R is vinyl or crotyl.

13. The compound of claim 1 wherein R is haloethyl.

14. The compound of claim 1 which is 1-hydroxy-2-propylsulfonyl-benzo-2,3,1-diazaborine or a non-toxic pharmaceutically acceptable salt thereof.

15. The compound of claim 14 wherein the propyl in the propylsulfonyl group attached to the 2-position of the benzo-2,3,1-diazaborine, is isopropyl.

16. The compound of claim 1 which is 1-hydroxy-2-butylsulfonly-benzo-2,3,1-diazaborine or a non-toxic pharmaceutically acceptable salt thereof.

17. The compound of claim 16 wherein the butyl in the butylsulfonyl group attached to the 2-position of the benzo-2,3,1-diazaborine, is isobutyl.

18. The compound of claim 1 which is 1-hydroxy-2-allylsulfonyl-benzo-2,3,1-diazaborine or a non-toxic pharmaceutically acceptable salt thereof.

19. The compound of claim 1 which is 1-hydroxy-2-chloromethyl sulfonyl-benzo-2,3,1-diazaborine or a non-toxic pharmaceutically acceptable salt thereof.

20. The compound of claim 1 wherein R is dichloropropyl.

21. A pharmaceutical composition which comprises an effective amount for controlling gram-negative bacteria of a compound of claim 1, or a pharmaceutically acceptable salt thereof, in combination with a pharmaceutically acceptable carrier.

22. The composition of claim 21 wherein R is chlorine substituted.

23. The composition of claim 21 wherein R' is an alkali metal cation.

24. The composition of claim 21 wherein the pharmaceutically active compound is a watersoluble salt.

25. The aqueous composition of claim 21 wherein the carrier is water.

26. A process of controlling gram-negative bacterial infections in warm-blooded mammals which comprises administering a therapeutically effective amount of a 1-hydroxy-benzo-2,3,1-diazaborine of claim 1, or a pharmaceutically acceptable water-soluble salt thereof, in combination with a pharmaceutically acceptable carrier to the mammal.

27. The compound of claim 11 wherein R is 2-methyl-propen-(1)-yl.

28. The compound of claim 11 wherein the halo is chloro.

29. The compound of claim 1 wherein R is 3-chloropropyl.

30. The compound of claim 1 where R' is a cation which together with and in formula I, is pharmaceutically acceptable in the control of gram-negative bacteria.

* * * * *